(12) United States Patent
Parikh et al.

(10) Patent No.: US 7,294,508 B2
(45) Date of Patent: Nov. 13, 2007

(54) ISOLATION OF INNER CELL MASS FOR THE ESTABLISHMENT OF HUMAN EMBRYONIC STEM CELL (HESC) LINES

(75) Inventors: Firuza Rajesh Parikh, Mumbai (IN); Satish Mahadoerao Totey, Mumbai (IN); Shailaja Anupam Saxena, Mumbai (IN)

(73) Assignee: Reliance Life Sciences Pvt. Ltd., Mumbai (IN)

( * ) Notice: Subject to any disclaimer, the term of this patent is extended or adjusted under 35 U.S.C. 154(b) by 642 days.

(21) Appl. No.: 10/226,711

(22) Filed: Aug. 23, 2002

(65) Prior Publication Data

US 2003/0104616 A1 Jun. 5, 2003
US 2007/0048864 A2 Mar. 1, 2007

Related U.S. Application Data

(60) Provisional application No. 60/314,323, filed on Aug. 23, 2001.

(51) Int. Cl.
   C12N 5/00 (2006.01)
   C12N 5/02 (2006.01)
   C12N 5/08 (2006.01)
   C12N 15/00 (2006.01)
   A01N 1/00 (2006.01)

(52) U.S. Cl. .................. 435/325; 435/1.1; 435/366; 435/375; 435/377; 435/440; 800/24

(58) Field of Classification Search ............... 435/69.1, 435/320.1, 325, 455, 366, 375, 377; 800/21, 800/24, 25
See application file for complete search history.

(56) References Cited

U.S. PATENT DOCUMENTS

| 5,843,780 A | 12/1998 | Thomson | 435/363 |
|---|---|---|---|
| 6,200,806 B1 | 3/2001 | Thomson | 435/366 |
| 2002/0022268 A1 | 2/2002 | Xu | 435/366 |
| 2002/0068045 A1 | 6/2002 | Reubinoff | 424/937 |

FOREIGN PATENT DOCUMENTS

WO   WO 01/51616   7/2001

OTHER PUBLICATIONS

Tanaka et al, Laser-assisted blastocyst dissection and subsequent cultivation of embryonic stem cells in a serum/cell free culture system: applications and preliminary results in a murine model. J Transl. Med. 4:20, 2006.*
Antinori et al. (1994). Seventeen live births after the use of erbium-yytrium aluminum garnet laser in the treatment of male factor infertility. Hum. Reprod. 9:1891-6.
Boada et al (1998). Successful use of a laser for human embryo biopsy in preimplantation genetic diagnosis: Report of two cases. Journal of Assisted Reproduction and Genetics. 15(5):302-7.
Bongso et al. (1994). Isolation and culture of inner cell mass cells from human blastocysts. Hum. Reprod. 9(11):2110-17.
Cohen et al. (1990). Impairment of the hatching process following IVF in the human and improvement of implantation by assisting hatching using micromanipulation. Hum. Reprod. 5(10:7-13.
Depypere et al. (1988). Comparison of zona cutting and zona drilling as techniques for assisted fertilization in the mouse. J. Reprod. Fertil. 84:205-11.
Doetschman (1988). Establishment of hamster blastocyst derived embryonic stem (ES) cell. Developmental Biology 127:224-7.
Evans and Kaufman (1981). Establishment in culture of pluripotential cells from mouse embryo. Nature 292:154-6.
Evans et al. (1990). Derivation and preliminary characterization of pluripotent cell lines from porcine and bovine blastocyst. Theriogenology 33(1):125-8.
Feichtinger et al. (1992). Photoablation of oocytes zona pellucida by erbium-yag laser for in-vitro fertilisation in severe male infertility. Lancet 339:811.
Gordon (1988). Use of micromanipulation for increasing the efficiency of mammalian fertilization in vitro. Ann. N.Y. Acad. Sci. 541:601-13.
Gordon and Talansky (1986). Assisted fertilization by zona drilling: a mouse model for correction of oligospermia. J. Exp Zool. 239:347-54.
Germond et al. (1995). Microdissection of mouse and human zona pellucida using a 1.48-um diode laser beam: efficacy and safety of the procedure. Fertility and Sterility 64(3):604-11.
Gérmond et al. (1996). Improved fertilization and implantation rates after non-touch zona pellucida microdrilling of mouse oocytes with a 1.48 micron diode laser beam. Hum. Reprod. 11(5):1043-8.
Giles et al. (1993). Pluripotency of cultured rabbit inner cell mass cells detected by isozyme analysis and eye pigmentation of fetuses following injection into blastocysts or morulae. Molecular Reproduction and Development 36:130-8.
Graves and Moreadith (1993). Derivation and characterization of putative pluripotential embryonic stem cells from pre-implantation rabbit embryos. Molecular Reproduction and Development 36:424-33.
Hollis et al (1997). Zona Pellucida Microdrilling with a 1.48 mum diode laser. IEEE Engineering in Medicine and Biology 16(3):43-7.
Iannaccone et al. (1994). Pluripotent embryonic stem cells from the rat are capable of producing chimeras. Developmental Biology 163:288-92.
Martin (1981). Isolation of pluripotent cell lines from early mouse embryos cultured in medium conditioned with teratocarcinoma stem cells. Proc. Natl. Acad. Sci. USA. 78(12):7634-8.

(Continued)

Primary Examiner—Sumesh Kaushal
(74) Attorney, Agent, or Firm—Vinson & Elkins LLP

(57) ABSTRACT

A method for isolating an inner cell mass comprising the steps of immobilizing a blastocyst stage embryo having a zona pellucida, trophectoderm, and inner cell mass, creating an aperture in the blastocyst stage embryo by laser ablation, and removing the inner cell mass from the blastocyst stage embryo through the aperture. The aperture is through the zona pellucida and the trophectoderm. The laser ablation is acheived using a non-contact diode laser. The inner cell mass removed from the blastocyst stage embryo is used to establish human Embryonic Stem Cell lines.

33 Claims, 18 Drawing Sheets

OTHER PUBLICATIONS

Meinecke-Tillmann and Meinecke (1996). Isolation of ES-like cell lines from ovine and caprine pre-implantation embryo. J. Animal Breeding and Genetics 113:413-26.

Narula et al. (1996). Morphological development, cell number, and allocation of cells to trophectoderm and inner cell mass of in vitro fertilized and parthenogenetically developed buffalo embryos: the effect of IGF-I. Mol. Reprod. Dev. 44(3):343-51.

Neev et al. (1993). Opening of the mouse zona pellucida by laser without a micromanipulator. Hum. Reprod. 8(6):939-44.

Notarianni et al. (1991). Derivation of pluripotent, embryonic cell lines from the pig and sheep. J. Reprod. Fertil. Suppl. 43:255-60.

Notarianni et al. (1990). Maintenance and differentiation in culture of pluripotential embryonic cell lines from pig blastocysts. J. Reprod. Fertil. Supp. 41:51-6.

Parikh et al. (1996). Assisted hatching in an in vitro fertilization programme. J. Reprod. Fertil. Suppl. 50:121-5.

Reubinoff et al. (2000). Embryonic stem cell lines from human blastocysts: Somatic differentiation in vivo. Nat. Biotechnol. 18:299-304.

Rink et al. (1994). 1-48 um diode laser microdissection of the zona pellucida of mouse zygotes, Proceedings SPIE 2134A:412-22.

Rink K et al. (1996). Non-contact microdrilling of mouse zona pellucida with an objective-delivered 1.48 microns diode laser. Lasers Surg. Med. 18:52-62.

Sukoyan et al. (1992). Isolation and cultivation of blastocyst derived stem cell lines from American Mink(*Mustela vison*). Molecular Reproduction and Development 33:418-31.

Tarin and Handyside (1993). Embryo biopsy strategies for preimplantation diagnosis. Fertil. Steril. 59(5):943-52.

Thomson et al. (1998). Embryonic stem cell lines derived from human blastocysts. Science 282:1145-7.

Thomson et al. (1996). Pluripotent cell line derived from common marmoset (*Callithrix jacchus*) blastoysts. Biol. Reprod. 55:254-9.

Thomson et al. (1995). Isolation of a primate embryonic stem cell line. Proc. Natl. Acad. Sci. USA. 92(17):7844-8.

Thomson and Marshall (1998). Primate Embryonic Stem Cells. Current Topics in Developmental Biology. 38:133-65.

Xu et al. (2001). Feeder-free growth of undifferentiated human embryonic stem cells. Nat. Biotechnol. 19(10):971-4.

International Search Report, PCT/IN 02/00168, dated Dec. 12, 2002.

Obruca A, et al. (1994). Use of lasers in assisted fertilization and hatching. *Human Reproduction* 9(9):1723-1726.

Veiga A, et al. (1997). Laser blastocyst biopsy for preimplantation diagnosis in the human. *Zygote* 5:351-354.

* cited by examiner

ISOLATION OF INNER CELL MASS FOR THE ESTABLISHMENT OF HUMAN EMBRYONIC STEM CELL (HESC) LINES

RELATED APPLICATION

This application claims priority to the provisional application Ser. No. 60/314,323 filed on Aug. 23, 2001.

FIELD OF THE INVENTION

The present invention relates to a method of isolation of inner cell mass (ICM) derived from blastocyst stage mammalian embryo for establishing human embryonic stem cell (hESC) lines, using a non-contact diode laser technique.

BACKGROUND OF THE INVENTION

The isolation of human stem cells offers the promise of a remarkable array of novel therapeutics. Biologic therapies derived from such cells through tissue regeneration and repairs as well as through targeted delivery of genetic material are expected to be effective in the treatment of a wide range of medical conditions. Efforts to analyze and assess the safety of using human stem cells in the clinical setting are vitally important to this endeavor.

Embryonic stem (ES) cells are the special kind of cells that can both duplicate themselves (self renew) and produce differentiated functionally specialized cell types. These stem cells are capable of becoming almost all of the specialized cells of the body and thus, may have the potential to generate replacement cells for a broad array of tissues and organs such as heart, pancreas, nervous tissue, muscle, cartilage and the like.

Stem cells have the capacity to divide and proliferate indefinitely in culture. Scientists use these two properties of stem cells to produce seemingly limitless supplies of most human cell types from stem cells, paving the way for the treatment of diseases by cell replacement. In fact, cell therapy has the potential to treat any disease that is associated with cell dysfunction or damage including stroke, diabetes, heart attack, spinal cord injury, cancer and AIDS. The potential of manipulation of stem cells to repair or replace diseased or damaged tissue has generated a great deal of excitement in the scientific, medical and biotechnology investment communities.

ES cells from various mammalian embryos have been successfully grown in the laboratory. Evans and Kaufman (1981) and Martin (1981) showed that it is possible to derive permanent lines of embryonic cells directly from mouse blastocysts. Thomson et al., (1995 and 1996) successfully derived permanent cell lines from rhesus and marmoset monkeys. Pluripotent cell lines have also been derived from pre-implantation embryos of several domestic and laboratory animal species such as bovines (Evans et al., 1990) Porcine (Evans et al., 1990, Notarianni et al., 1990), Sheep and goat (Meinecke-Tillmann and Meinecke, 1996, Notarianni et al., 1991), rabbit (Giles et al., 1993, Graves et al., 1993) Mink (Sukoyan et al., 1992) rat (Iannaccona et al., 1994) and Hamster (Doetschman et al., 1988). Recently, Thomson et al (1998) and Reubinoff et al (2000) have reported the derivation of human ES cell lines. These human ES cells resemble the rhesus monkey ES cell lines.

ES cells are found in the ICM of the human blastocyst, an early stage of the developing embryo lasting from the $4^{th}$ to $7^{th}$ day after fertilization. The blastocyst is the stage of embryonic development prior to implantation that contains two types of cells viz.

1. Trophectoderm: outer layer which gives extra embryonic membranes.
2. Inner cell mass (ICM): which forms the embryo proper.

In normal embryonic development, ES cells disappear after the $7^{th}$ day and begin to form the three embryonic tissue layers. ES cells extracted from the ICM during the blastocyst stage, however, can be cultured in the laboratory and under the right conditions proliferate indefinitely. ES cells growing in this undifferentiated state retain the potential to differentiate into cells of all three embryonic tissue layers. Ultimately, the cells of the inner cell mass give rise to all the embryonic tissues. It is at this stage of embryogenesis, near the end of first week of development, that ES cells can be derived from the ICM of the blastocyst.

The ability to isolate ES cells from blastocysts and grow them in culture seems to depend in large part on the integrity and condition of the blastocyst from which the cells are derived. In short, the blastocyst that is large and has distinct inner cell mass tend to yield ES cells most efficiently. Several methods have been used for isolation of inner cell mass (ICM) for the establishment of embryonic stem cell lines. Most common methods are as follows:

1. Natural Hatching of the Blastocyst:

In this procedure blastocyst is allowed to hatch naturally after plating on the feeder layer. The hatching of the blastocyst usually takes place on day 6. The inner cell mass (ICM) of the hatched blastocyst develops an outgrowth. This outgrowth is removed mechanically and is subsequently grown for establishing embryonic stem cell lines. However, this procedure has few disadvantages. Firstly, Trophectoderm cells proliferate very fast in the given culture conditions and many a times, suppress the outgrowth of inner cell mass. Secondly, while removing the outgrowth of the inner cell mass mechanically, there is a chance of isolating trophectoderm cells. Thirdly, the percentage of blastocysts hatching spontaneously in humans is very low.

2. Microsurgery:

Another method of isolation of inner cell mass is mechanical aspiration called microsurgery. In this process, the blastocyst is held by the holding pipette using micromanipulator system and positioned in such a way that the inner cells mass (ICM) is at 9 O'Clock position. The inner cell mass (ICM) is aspirated using a biopsy needle which is beveled shape and is inserted into the blastocoel cavity. This procedure too is disadvantageous as the possibility to isolate the complete inner cell mass is low and many a time cells get disintegrated. It is a very tedious procedure and may cause severe damage to the embryo. The operation at the cellular level requires tools with micrometer precision, thereby minimizing damage and contamination.

3. Immunosurgery:

This is a commonly used procedure to isolate inner cell mass (ICM). The inner cell mass (ICM) is isolated by complement mediated lysis. In this procedure, the blastocyst is exposed either to acid tyrode solution or pronase enzyme solution in order to remove the zona pellucida (shell) of blastocyst. The zona free embryo is then exposed to human surface antibody for about 30 min to one hour. This is followed by exposure of embryos to guinea pig complement in order to lyse the trophectoderm. This complement mediated lysed trophectoderm cells are removed from inner cell mass (ICM) by repeated mechanical pipetting with a finely drawn Pasteur pipette. All the embryonic stem cell lines reported currently in the literature have been derived by this method. However, this method has several disadvantages.

Firstly, the embryo is exposed for a long time to acid tyrode or pronase causing deleterious effects on embryo, thereby reducing the viability of embryos proper. Secondly, it is time consuming procedure as it takes about 1.5 to 2.0 hours. (Narula et al.,1996). Thirdly, the yield of inner cell mass (ICM) per blastocyst is low. Fourthly, critical storage conditions are required for antibody and complement used in the process. Lastly, it involves the risk of transmission of virus and bacteria of animal origin to humans, as animal derived antibodies and complement are used in the process. In this process, two animal sera are used. One is rabbit antihuman antiserum and the other is guinea pig complement sera.

The human cell lines studied to date are mainly derived by using a method of immunosurgery, where animal based antisera and complement was used.

Other possible disadvantages of the existing cell lines are as follows:
1. Use of feeder cells for culturing the human embryonic stem cell (hESC) lines produces mixed cell population that require the Embryonic stem cells (ESC) to be separated from feeder cell components and this impairs scale up.
2. Embryonic stem cells (ESC) get contaminated by transcripts from feeder cells and cannot be used on a commercial scale. It can be used only for research purposes.

Geron established a procedure where human Embryonic Stem Cell (hESC) line was cultured in the absence of feeder cells (XU et.al 2001). The hESC were cultured on an in an undifferentiated state. The hESC contained no xenogenic components of cancerous origin from other cells in the culture. Also, the production of hESC cells and their derivatives were more suited for commercial production. In this process, there was no need to produce feeder cells on an ongoing basis to support the culture, and the passaging of cells could be done mechanically. However, the main disadvantage of this procedure is that the inner cell mass (ICM) is isolated by immunosurgery method, wherein the initial derivation of Embryonic Stem Cells is carried out using feeder layer containing xenogenic components. This raises the issue of possible contamination with animal origin viruses and bacteria.

In order to simplify the procedure of inner cell mass isolation and to make it safe, the scientists of the present invention have come out with a novel method of isolation of the inner cell mass using a non-contact laser, wherein, the use of animal based antisera and complement have been eliminated.

Use of Laser Technique in Assisted Reproduction:

With the advent of assisted reproductive technologies (ART), several methods have been used for improving fertilization, facilitating blastocyst hatching (Cohen et al, 1990) and performing blastomere biopsy (Tarin and Handyside, 1993). Commonly used methods are chemical (Gordon and Talansky 1986), mechanical (Depypere et al., 1988) and laser (Feichtinger et al., 1992) so as to produce holes in the zona pellucida (Gordon, 1988). Recently, an infrared 1.48 μm diode laser beem focused through a microscope objective was shown to allow rapid, easy and non-touch microdrilling of mouse and human zona pellucida and high degree of accuracy was maintained under conventional culture conditions (Rink et al., 1994). The drilling effect was shown due to a highly localized heat-dependent disruption of the zona pellucida glycoprotein matrix (Rink et al., 1996). Contrary to the detrimental effect on compacted mouse embryos induced by the 308 nm xenon-chlorine excimer laser (Neev et al., 1993), the drilling process in the infrared region did not affect embryo survival in mice (Germond et al., 1995) or in humans (Antinori et al., 1994).

Currently, lasers are being investigated as a tool to aid fertilization and in assisted hatching. Recent reports show that use of 1.48 μm diode laser for microdrilling mouse zona pellucida is highly safe and does not affect neuro-anatomical and neurochemical properties in mice and also improves fertilization (Germond et al., 1996). Obruca and colleagues first reported the success of laser-assisted hatching in human IVF in 1994. In this study, a 20- to 30-micron hole made in the zona pellucida (ZP) when the Patients with previous IVF failures from two separate centers were included in this study. There was a higher implantation rate per embryo in the laser-assisted hatching group (14.4%) versus the control group (6%). Pregnancy rates per transfer were also improved (40% versus 16.2%).

In a separate study, Er:YAG laser was used to thin the ZP of embryos derived from patients undergoing repeated IVF. Using a laser for thinning the ZP, embryologists are able to achieve accurate reduction of the ZP by 50%, which is very difficult with acidic Tyrode's solution. Presence of Acid Tyrode's solution near the embryo may also be detrimental. The rate of clinical pregnancies in the laser-hatched group was 42.7%, as compared to 23.1% in the control unhatched group. Since this data looked promising, the indication of laser-assisted hatching was extended. Women undergoing IVF for the first time yielded 39.6% clinical pregnancy rate in the laser-treated group versus a 19% rate in the control unhatched group (Parikh et al 1996).

During the last decade there has been ongoing research on the isolation of inner cell mass (ICM), as it is useful in establishing embryonic stem cell lines which in turn have the ability to develop into most of the specialized cells in the human body including blood, skin, muscle and nerve cells. They also have the capacity to divide and proliferate indefinitely in culture.

The present invention involves the isolation of inner cell mass (ICM), using laser ablation technique without undergoing the cumbersome procedure of immunosurgery. Hence, in the present invention, the use of animal derived antibodies or sera are eliminated and the procedure is safe, simple, rapid, and commercially viable.

The present invention, obviates the shortcomings associated with the conventional methods of isolation of inner cell mass (ICM). The inner cell mass (ICM) isolated by the present invention is found to be intact without causing any destruction or damage to the cells. The present invention thus provides a quick reliable and non-invasive method for isolation of inner cell mass (ICM). It also completely ruptures the trophectoderm thereby minimizing the contamination of inner cell mass (ICM), thus ensuring the purity of inner cell mass (ICM).

REFERENCES

1. Antinori S, Versaci C, Fuhrberg P et al (1994). Seventeen live birth after the use of erbium-yytrium aluminum garnet laser in the treatment of male factor infertility. Hum Reprod. 9: 1891-1896.
2. Cohen J, Elsner C, Kort H et al (1990). Impairment of the hatching process following IVF in the human and improvement of implantation by assisting hatching using micromanipulation. Hum Reprod. 5: 7-13
3. Depypere H T, McLaughlin K J, Seamark R F et al (1988). Comparison of zona cutting and zona drilling as techniques for assisted fertilization in the mouse. J. Reprod Fertil. 84: 205-211.

4. Doetschman T. Williams P and Maeda N (1988) Establishment of hamster blastocyst derived embryonic stem (ES) cell. Developmental Biology 127: 224-227.
5. Evans M J and Kaufman M H (1981). Establishment in culture of pluripotential cells from mouse embryo. Nature 292: 154-156.
6. Evans M J, Notarianni E, Laurie S and Moor R M (1990) Derivation and preliminary characterization of pluripotent cell lines from porcine and bovine blastocyst. Theriogenology 33: 125-128.
7. Feichtinger W, Strohmer H, Fuhrberg P et al (1992). Photoablation of oocyte zona pellucida by erbium-yag laser for in-vitro fertilization in severe male infertility- .Lancet. 339, 811.
8. Gordon J W (1988). Use of micromanipulation for increasing the efficiency of mammalian fertilization in vitro. Ann. N.Y. Acad.Sci. 541: 601-613.
9. Gordon J W and Talansky B E (1986). Assisted fertilization by zona drilling: a mouse model for correction of oligospermia. J. Exp Zool. 239: 347-354.
10. Germond M, Nocera D, Senn A. Rink K. et al (1995). Microdissection of mouse and human zona pellucida using 1.48 microns diode laser beam: efficacy and safety of the procedure. Fertil Steril. 64: 604-611.
11. Germond M, Nocera D, Senn A, Rink A et al (1996). Improved fertilization and implantation rates after non-touch zona pellucida microdrilling of mouse oocytes with a 1.48 micron diode laser beam. Hum Reprod. 11: 1043-1048
12. Giles J R, Yang X, Mark X and Foot R H (1993). Pluripotency of cultured rabbit inner cell mass cells detected by isozyme analysis and eye pigmentation of fetus following injection into blastocysts or morula. Molecular Reproduction and Development 36: 130-138.
13. Graves K H and Moreadith R W (1993). Derivation and characterization of putative pluripotential embryonic stem cells from pre-implantation rabbit embryo. Molecular reproduction and Development 36: 424-433.
14. Iannaccone P M, Taborn G U, Garton R L et al (1994). Pluripotent embryonic stem cells from the rat are capable of producing chimeras. Developmental Biology 163:288-292.
15. Martin G R (1981) Isolation of pluripotent cell lines from early mouse embryos cultured in medium conditioned with teratocarcinoma stem cells. Proceeding of National Academy of Sciences USA 72: 1441-1445.
16. Meinecke-Tillmann S and Meinecke B (1996). Isolation of ES like cell lines from ovine and caprine pre-implantation embryo. J Animal Breeding and Genetics 113: 413-426.
17. Narula A, Taneja, Totey S M (1996) Morphological cells to trophectoderm inner cell mass of in vitro fertilized and parthenogenetically developed buffalo embryo: the effect of IGF-I. Mol. Reprod. Dev. 44(3):343-51.
18. Neev J, Gonzales A, Lucciardi F et al (1993). Opening of the mouse zona pellucida by laser without a micromanipulator. Hum Reprod. 8: 939-944.
19. Obruca A, Strohmer H, Sakkas D (1994). Use of laser in assisted fertilization and hatching. Hum Reprod. 9:1723-1726.
20. Parikh F R, Kamat S A, Nadkarni S et al (1996). Assisted hatching in an in vitro fertilization program. J Reprod Fertil Suppl 50: 121-125.
21. Reubinoff B E, Per M F, Fong C Y, Trounson A and Bongso A (2000) Embryonic stem cell lines from human blastocysts: Somatic differentiation in vivo. Nat Biotechnol. 18:299-304.
22. Rink K, Delacretaz G, Salathe R P et al (1994). Proceedings SPIE. 2134A, 412-422.
23. Rink K, Delacretaz G, Salathe R P et al (1996). Non-contact microdrilling of mouse zona pellucida with an objective delivered 1.48 microns diode laser. Lasers Surg Med. 18:52-62.
24. Sukoyan M A, Golublitsa A N, Zhelezova A I et al (1992) Isolation and cultivation of blastocyst derived stem cell lines from American Mink. Molecular Reproduction and Development 33: 418-431.
25. Tarin J J and Handyside A H (1993). Embryo biopsy strategies for preimplantation diagnosis. Fertil Steril 59:943-952.
26. Thomson J A, Itskovitz-Eldor J, Shapiro S S. et al. (1998). Embryonic stem cell lines derived from human blastocyst. Science 282: 1145-1147.
27. Thomson J A, Kalishman J, Golos T G et al (1996). Pluripotent cell line derived from common marmoset blastocyst. Biology of Reproduction. 55: 254-259

OBJECTS OF THE INVENTION

1. It is an object of the present invention, to develop a process of isolation of inner cell mass, using laser ablation technique, without undergoing the cumbersome procedure of immunosurgery.
2. It is another object of the present invention to isolate ICM using laser ablation technique without using any animal generated antibodies and sera, thereby preventing the possibility of transmission of animal organism to human and thus can safely be used on commercial scale.
3. It is another object of the present invention to isolate inner cell mass (ICM) from blastocyst stage of a mammalian embryo using a non-contact diode laser.
4. It is another object of the present invention to isolate inner cell mass (ICM) by simple, shorter and easily feasible way without affecting/destroying the inner cell mass (ICM).
5. It is still another object of the present invention to ensure the purity of inner cell mass (ICM) by rupturing completely trophectoderm thereby minimising the contamination of inner cell mass (ICM).
6. It is still another object of the present invention to isolate inner cell mass (ICM) of high yield and purity as compared to the inner cell mass (ICM) isolated by the conventional methods.

These and other objects of the invention will become more readily apparent from the ensuing description.

DETAILS OF INVENTION

The present invention relates to isolation of inner cell mass, using laser ablation of zona pellucida (ZP) and trophectoderm (TE) and aspiration of inner cell mass for establishing embryonic stem cell lines. In the present invention, the non contact diode laser used is highly accurate and reliable tool for cellular microsurgery. The system incorporates the latest in fiber optic technology to provide the most compact laser system currently available. The 1.48 μm diode non-contact Saturn Laser System is mounted/implanted via the epifluorescence port to inverted microscope fitted with micromanipulators. A pilot laser is used to target the main ablation laser and a series of LEDs inform the user when the laser is primed and is ready to fire. A two-second-operation window is used to reduce the possibility of accidentally firing the laser. The spot diameter of the laser can be varied according to the hole size required.

Couples undergoing in vitro fertilization (IVF) treatment voluntarily donate surplus human embryos. These embryos are used for research purposes after taking the written, voluntary consent from these couples. In the present invention, blastocyst stage embryos are taken for the isolation of inner cell mass. The blastocyst is placed in a 35 mm petridish in a 50 micro litre droplets of Ca++/Mg++ free embryo biopsy medium and is covered with mineral oil. The micromanipulator is set up to perform the embryo biopsy procedure. The blastocyst is placed in embryo biopsy medium and the petridish containing the blastocyst is placed on the heating stage of the microscope. The blastocyst is positioned at the center of the field. The blastocyst is immobilized on to the holding pipette in such a way that the inner cell mass is at 3 O'Clock position. The zona pellucida and trophectoderm close to inner cell mass is positioned on the aiming spot of the laser beam. A small portion of zona pellucida and trophectoderm is laser ablated. Biopsy pipette is then gently inserted through the hole in the zona pellucida and trophectoderm and the inner cell mass is gently aspirated. After isolation of the complete inner cell mass, the cells are given several washes with embryonic stem cell (ESC) medium. The cells are then plated on to feeder layer with embryonic stem cell medium for establishing embryonic stem cell lines. The embryonic stem cells were then characterized for cell surface markers such as SSEA-1, SSEA-3, SSEA-4, TRA-1-60, TRA-1-81, OCT-4 and alkaline phosphatase. The embryonic stem cell lines are also karyotyped.

a) Development of Blastocyst in Vitro:

Institutional Ethics Committee approval has been obtained before initiation of this study. Prior written consent was taken from individual donor for the donation of surplus embryos for this study after completion of infertility treatment.

Protocol generally used for infertility patients for obtaining viable embryo is as follows:

The ovarian superovulation began with gnRH agonist analog suppression daily starting in the mid-luteal phase and administered in doses of 500-900 mgs for about 9-12 days. Ovarian stimulation was started after adequate ovarian suppression with human menopausal gonadotropins (hMG) or recombinant follicle stimulating hormone (FSH) (Gonal-F, Recagon) in appropriate doses depending on the age and ovarian volume. The dose was also adjusted as necessary to produce controlled ovarian stimulation. Serum beta-estradiol (E2) measurements were carried out as required. Vaginal ultrasound was performed daily from cycle day 7 onward. Human Chorionic gonadotropin 5000-10000 I.U. was administered when three or more follicles were at least 17 mm in largest diameter. Transvaginal aspiration was performed 34-36 h later. Oocytes were then subjected to intracytoplasmic sperm injection.

A glass holding pipette 40-60 μm in diameter was used to secure the egg. Motile sperm were placed in a drop of polyvinyl pyrolidone (PVP) solution and overlaid with mineral oil. An injection needle with an outer diameter of roughly 5-6 μm and inner diameter 3-4 μm was used to pierce the zona pellucida at about 3 O'Clock position, The selected spermatozoon was immobilized by cutting the tail with the injection micropipette. The holding pipette secured the oocyte and spermatozoon was injected directly into the center of the oocyte.

Oocytes were checked after 16-18 hours of culture for fertilization. At this point the fertilized oocyte had pronuclei (also called one cell embryo). One-cell embryos were then transferred into pre-equilibrated fresh ISM-1 medium and incubated at 37° C. in a 5% CO2 in air. The next day embryos were transferred into ISM-2 medium. Every alternate day embryos were transferred into fresh ISM-2 medium. From day 5 onward embryos were checked for the blastocyst development. After the treatment is over, the surplus blastocysts were donated by the couples for this research work.

b) Setting up of the Laser:

The present invention relates to describing a unique method for inner cell mass isolation for establishment of embryonic stem cells using the non-contact diode laser. The laser is highly accurate and reliable tool for cellular microsurgery. The system incorporates the latest in fiber optic technology to provide the most compact laser system currently available. The 1.48 μm diode non-contact Saturn Laser System was mounted via the epifluorescence port to Zeiss inverted microscope fitted with micromanipulators.

A pilot laser was used to target the main ablation laser and a series of LED's inform the user when the laser is primed and ready to discharge the laser beam. A two-second-operation window was used to reduce the possibility of accidentally firing the laser. The spot diameter of the laser can be varied according to the ablation size required.

c) Laser Ablation and Isolation of Inner Cell Mass.

The blastocyst stage embryo was individually placed in a 50 μl drop of biopsy medium ($Ca^{++}/Mg^{++}$ free) in a 35-mm petri dish. The embryo was immobilized on to the holding pipette in such a way that the inner cell mass remained at 3 O'Clock position and the zona pellucida and trophectoderm close to inner cell mass positioned on the aiming spot. A continuous 1.48 μm diode laser was used to aperture the Zona Pellucida (ZP), which is a glycoprotein layer protecting the oocyte. At this wavelength, the hole was induced by a local thermo-dissolution of the glycoprotein matrix. Once the zona pellucida was dissolved, trophectoderm cells were ablated by giving 3 pulses to cause photolysis. After ablation of both zona pellucida and trophectoderm, the aspiration pipette was introduced through laser-ablated hole and ICM was removed by gentle aspiration, having an internal diameter of 30-35 microns.

d) Culturing of Human Embryonic Stem Cells (hESC)

Prior to culturing, the aspirated ICM was washed thoroughly in ES medium, which medium was found to be preferred for isolation of embryonic stem cell lines. Given below is the procedure when the invention was carried out using feeder layer. In this process, the inner cell mass was cultured in 96 well plate in the presence of mouse inactivated embryonic fibroblast feeder layer. Embryonic fibroblast feeder layer was preferably obtained from 12.5 to 13.5 day old C57BL/6 mice or C57BL/6XSJL F-1 mice or out bred CD1 mice or from human amniotic fluid-and used as a feeder layer. Embryonic fibroblast feeder layer was inactivated by gamma irradiation (3500 rads). The mouse embryonic fibroblast feeder layer was cultured on 0.5% gelatin coated plate with ES medium consisting of Dulbecco's modified Eagle's medium without Sodium pyruvate with high glucose contain (70-90%), Fetal bovine serum (10-30%), beta-mercaptoethanolm (0.1 mM), non-essential amino acids (1%), L-Glutamine 2 mM, basic fibroblast growth factor (4 ng/ml). Inner cell mass was then plated on mouse inactivated embryonic fibroblast. After 4-7 days, ICM derived masses were removed from outgrowth with sterile fire polished pipette and were dissociated mechanically and plated on fresh feeder cells. Further dissociation was carried out with 0.5% trypsin-EDTAm supplemented with 1% chicken serum.

Established cell lines were karyotyped and characterized for several surface markers such as SSEA-1, SSEA-3, SSEA-4, OCT-4, Alkaline phosphatase, TRA-1-81, TRA-1-60 as described by Thomson et al., (1998), reubinoff et al., (200).

The following examples are intended to illustrate the invention but do not limit the scope thereof.

Example 1

Total of 24 blastocyst stage human embryos were used for the isolation of inner cell mass. Embryos were washed several times in blastocyst culture medium (ISM-2 medium, Medicult, Denmark). Individual blastocyst was then placed in the 50 µl drop of Ca++/Mg++ free embryo biopsy medium(EB 10 medium, Scadinavian). Micro drops were covered with mineral oil. Micromanipulator was set up. A glass holding pipette with outer diameter 75 µm and inner diameter 15 µm was used to secure the embryo. Biopsy pipette with an outer diameter of roughly 49 µm and inner diameter 35 µm was used for aspiration of inner cell mass. A pilot laser was used to target the main ablation laser. Embryo was immobilized on to the holding pipette in such a way that inner cell mass remained at 3 O'clock position and the zona pellucida and trophectoderm close to inner cell mass positioned to the aiming spot. The hole was induced by a local thermo-dissolution of the zona. Trophectoderm cells were ablated by giving 3 pulses to cause photolysis. After ablation of both the zona pellucida and trophectoderm, the biopsy pipette was introduced through laser ablated hole and inner cell mass was removed. Inner cell mass was then washed several times in ES medium and placed in 96 well dish in the presence or absence of feeder cells. The following data is presented in the tablular form.

TABLE 1

Summary of hESC lines developed using Laser ablation Technique of the present invention with the use of mouse feeder cells.

| No. of blastocyst used for laser ablation | Total inner cell mass removed | With mouse feeder cells | |
|---|---|---|---|
| | | No. of ICM used | No of ES cell lines established |
| 24 | 18 | 14 | 4 |

Similarly, an experiment was conducted with conventional method of isolation of inner cell mass i.e. using immunosurgery and may be reported as follows:

Example 2

The objective was to determine efficiency of isolation of inner cell mass with conventional method I.e. immunosurgery and compared with newly invented laser ablated method.

21 blastocyst stage human embryo were used for isolation of inner cell mass. Embryos were washed several times with blastocyst culture medium (ISM-2 medium) and followed by ES medium. Individual blastocyst stage embryo was then placed in 50 µl micodrops of 1:50 anti-human antibody (Sigma) for 30 minutes at 37° C. and 5% $CO_2$ in air. Blastocyst stage embryos were then washed four times after incubation with ES medium. Blastocysts were then again placed in 50 µl of microdrops of guinea pig complement at the concentration of 1:10 for 10 minutes at 37° C. and 5% $CO_2$ in air. After incubation blastocyst stage embryos were washed several times in ES medium using fine bore glass pipette in order to remove trophectoderm. Isolated inner cell mass was then washed with ES medium and cultured in 96 well plate in the presence or absence of feeder cells. Data are presented in the table:

TABLE 2

Summary of hESC lines developed using immunosurgery with/without the use of mouse feeder cells.

| No. of blastocyst used for laser ablation | Total Inner cell mass removed | With mouse feeder cells | | Without mouse feeder cells | |
|---|---|---|---|---|---|
| | | No. of ICM used | No of ES cell lines established | No. of ICM used | No. of ES cell lines established |
| 21 | 14 | 12 | 3 | 2 | 0 |

Although the isolation of inner cell mass using both the methods did not show any significant difference, however, of isolation of inner cell mass by laser ablation has distinct advantage. This method will eliminate the use of antibodies and sera of animal origin. Isolation of inner cell mass by laser ablation method can be further cultured in the presence or absence of feeder layer. However, culturing of inner cell mass in a feeder free condition will further eliminate the possibilities of contamination of ES cell lines with animal viruses or bacteria and can be commercially utilized for human transplantation studies. In the current experiments, efforts were made to establish ES cell line in the absence of feeder cells.

A preferred embodiment of the invention is illustrated in the accompanying drawings.

FIG. 1(a) to 1(g) of the present invention, pertains to the isolation of inner cell mass (ICM) from the blastocyst of one embryo and FIG. 2(a) to 2(g) pertains to the isolation of inner cell mass (ICM) from the blastocyst of another embryo. FIG. 3,4, and 5 pertains to culturing of ICM on feeder cells at different stages.

FIG. 1. (a) is a scanned image of human blastocyst, secured with glass holding pipette such that the ICM is at 3 O'Clock position.

FIG. 1 (c) is a scanned image of aspiration pipette close to the blastocyst following zona and trophectoderm ablation.

FIG. 1 (d) is a scanned image of beginning of aspiration of ICM with aspiration pipette.

FIG. 1 (e) is a scanned image of large portion of ICM in the aspiration pipette during aspiration process.

FIG. 1 (f) is a scanned image of the ICM after removing from the blastocyst.

FIG. 1 (g) is a scanned image of the remaining trophectoderm and zona pellucida remaining after ICM isolation.

FIG. 2 (b) is a scanned image of slight protrusion of inner cell mass after zona and trophectoderm is laser ablated.

FIG. 2 (c) is a scanned image of the aspiration pipette being position close to the ICM after ablating the zona and neighboring trophectoderm cells with laser.

FIG. 2 (d) is a scanned image of ICM being aspirated with the aspiration pipette by gentle suction.

FIG. 2 (e) is a scanned image of large portion of ICM in the aspiration pipette.

FIG. 2 (f) is a scanned image of the ICM after removing from the blastocyst.

FIG. 2 (g) is a scanned image of the trophectoderm and zona pellucida left after the isolation of ICM from the blastocyst.

Figure 1A:
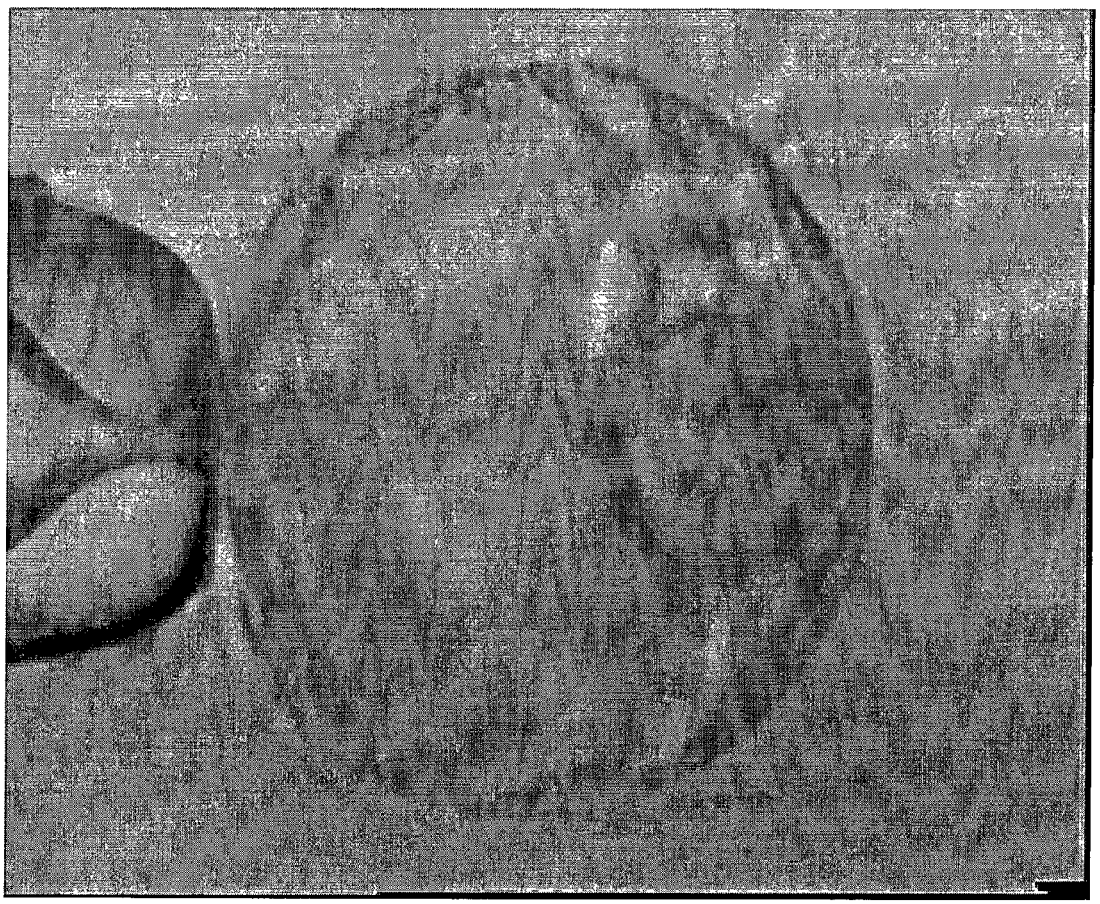
FIG. 1 (b) is a scanned image wherein part of zona pellucida and trophectoderm ablated with laser (arrow).
Figure 1B:
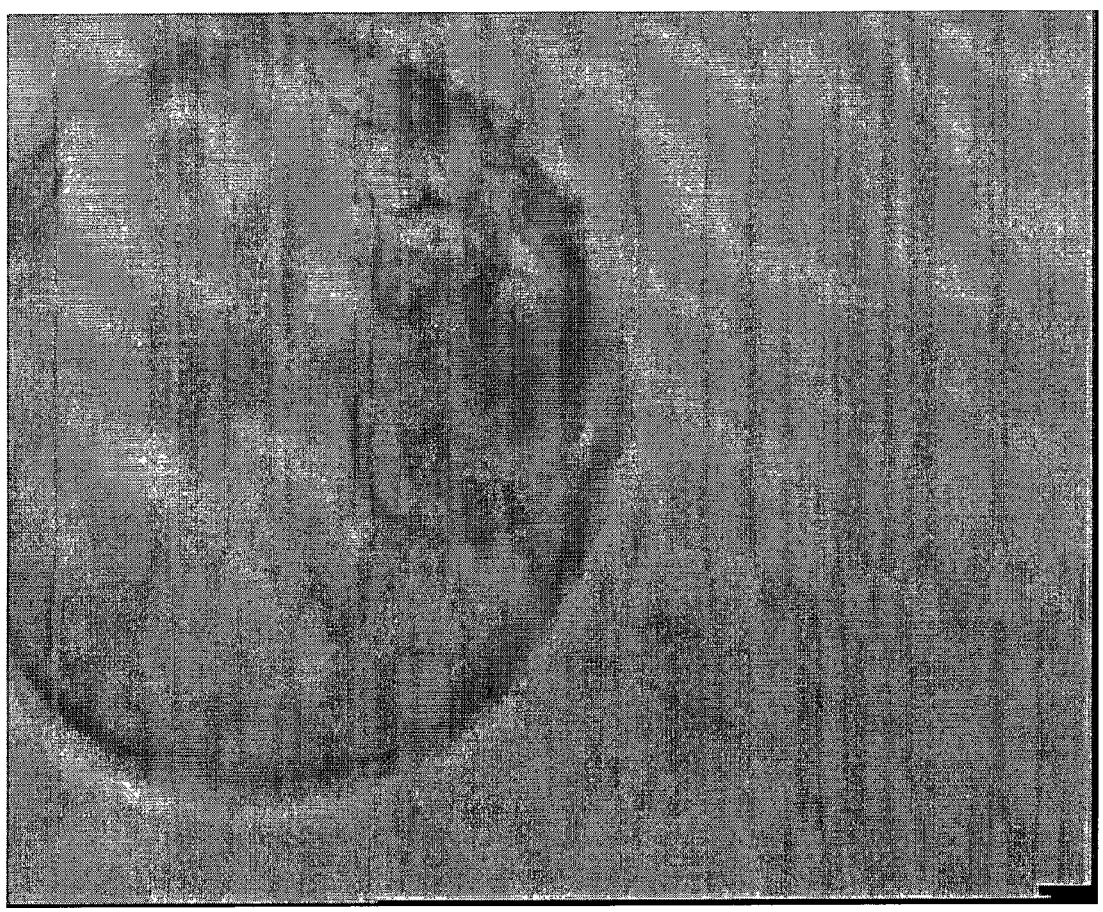
Figure 1C:
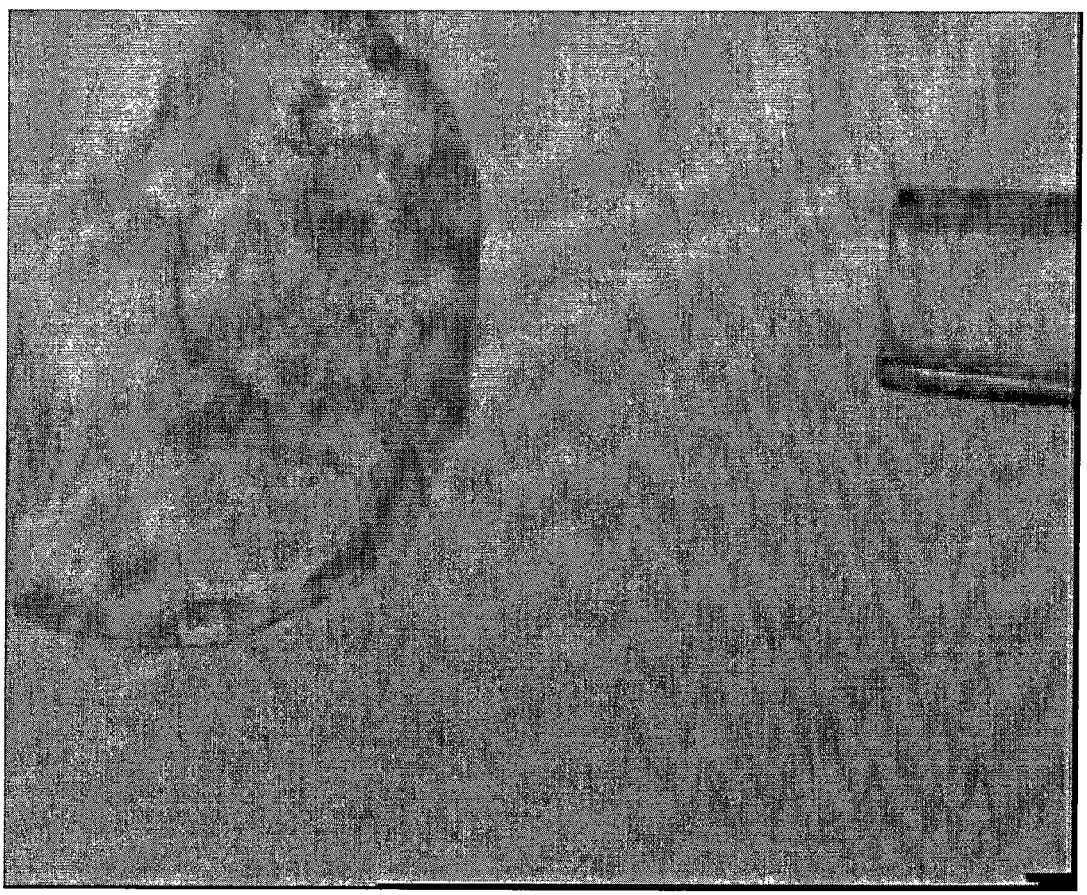
Figure 1D:
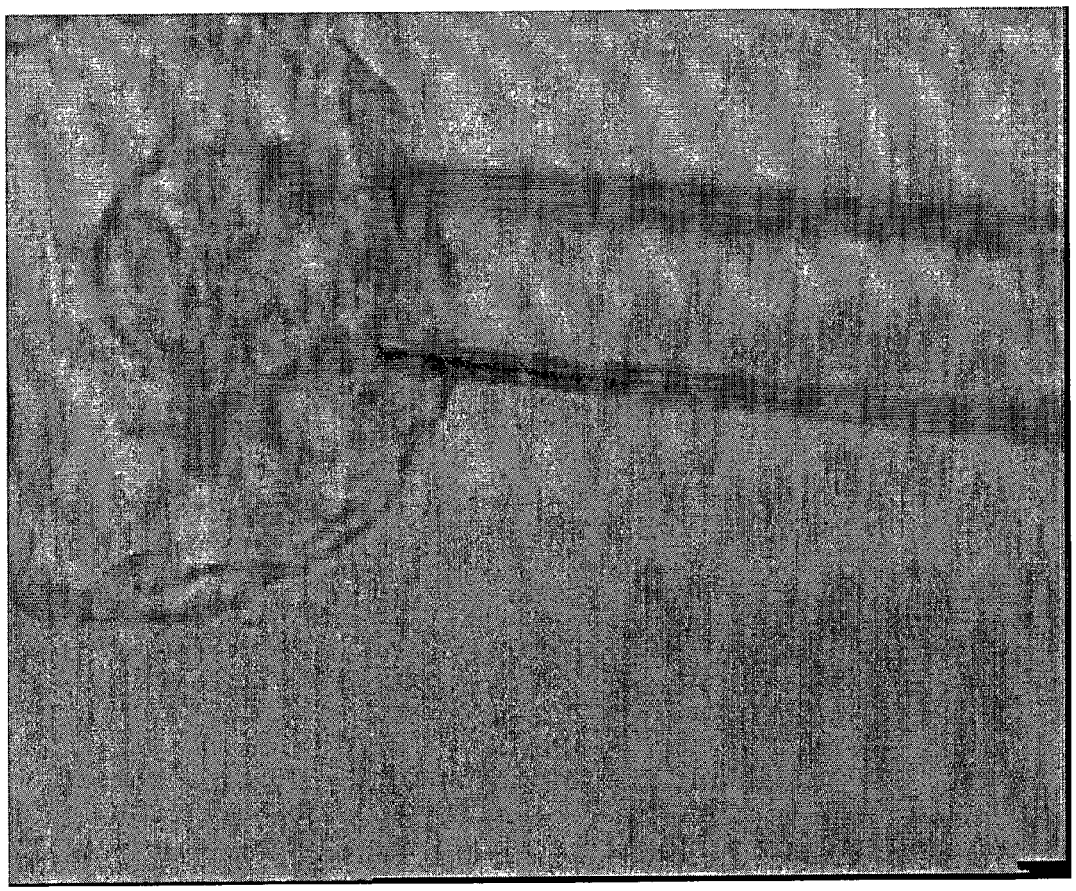
Figure 1E:
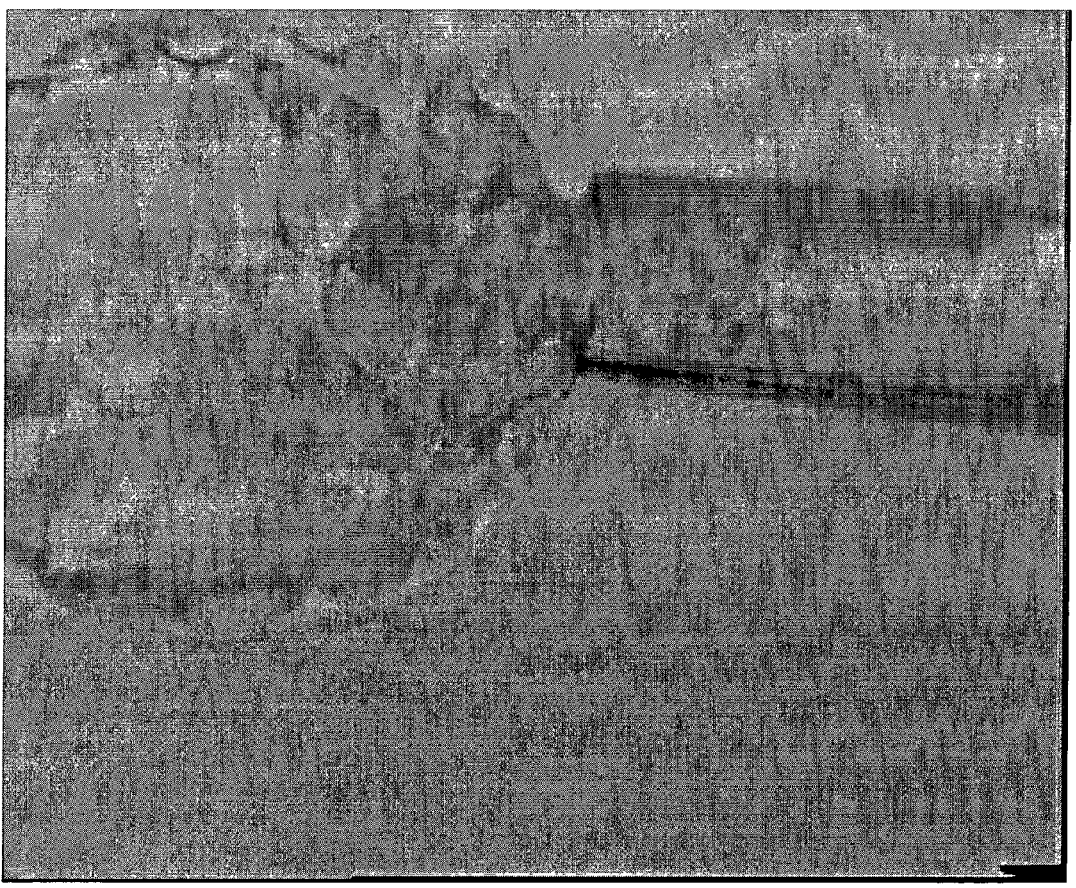
Figure 1F:
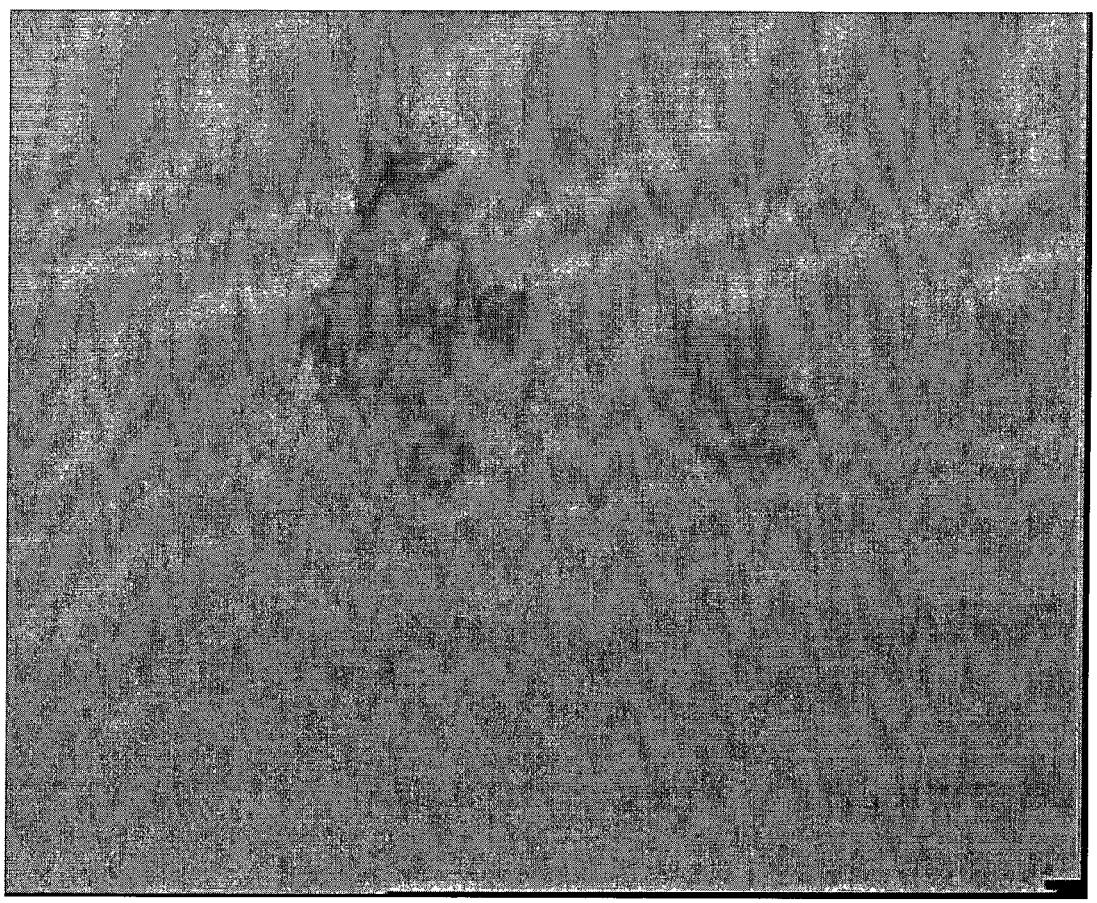
Figure 1G:
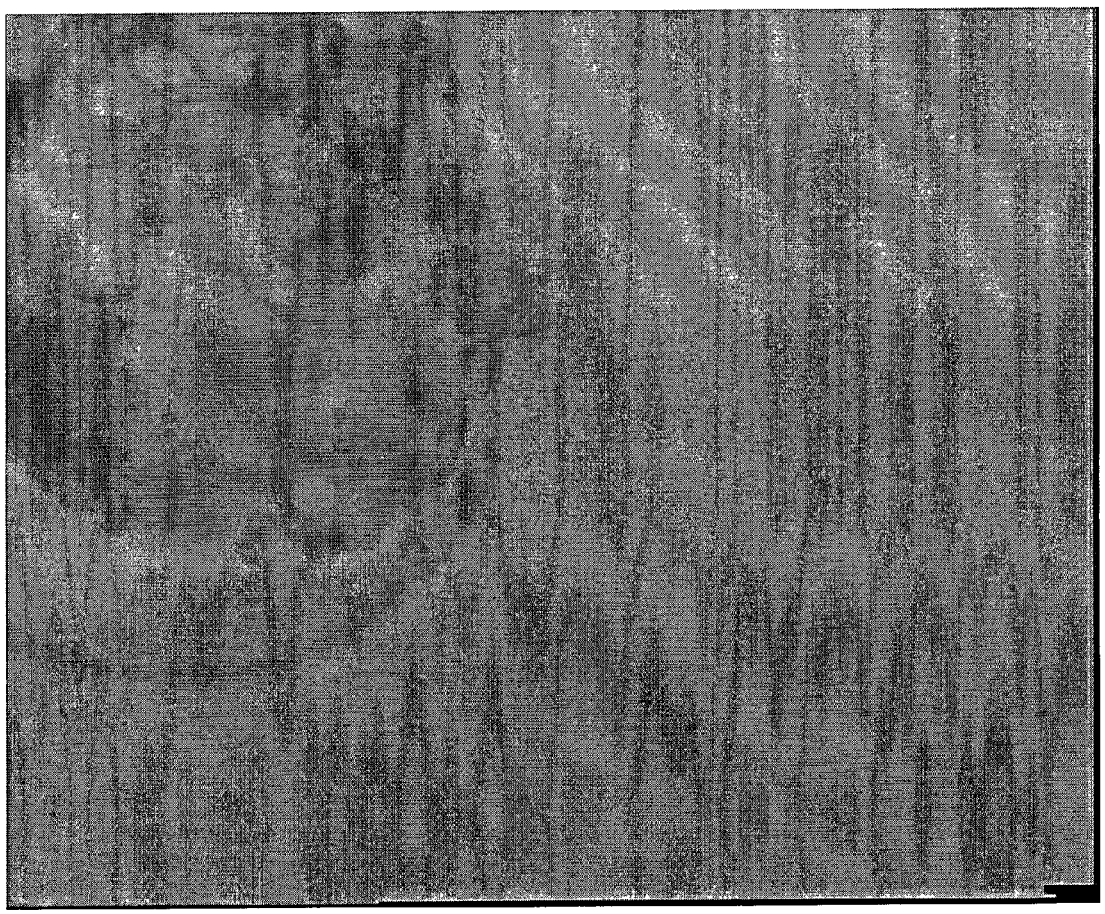
Figure 2:
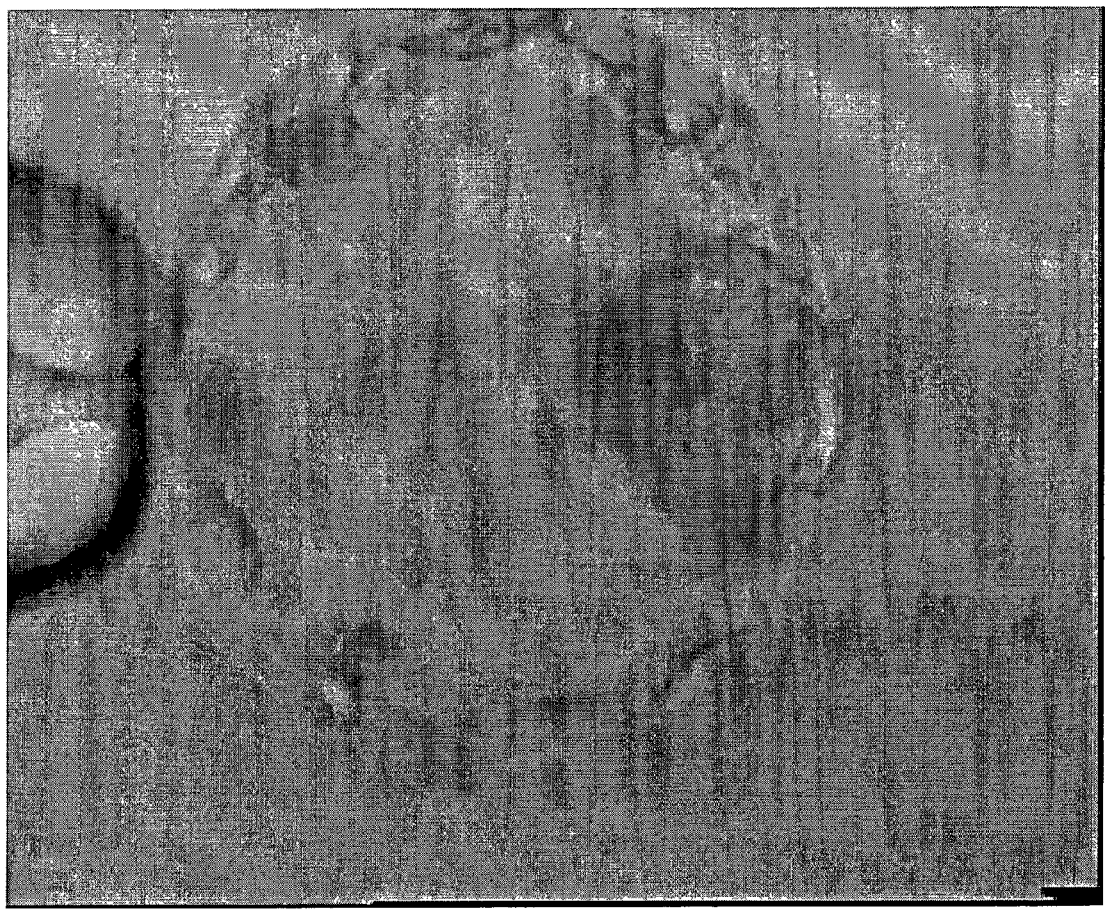
FIG. 2 (a) is a scanned image of another human blastocyst, secured with glass holding pipette such that the ICM is at 3 O'Clock position.
Figure 2B:
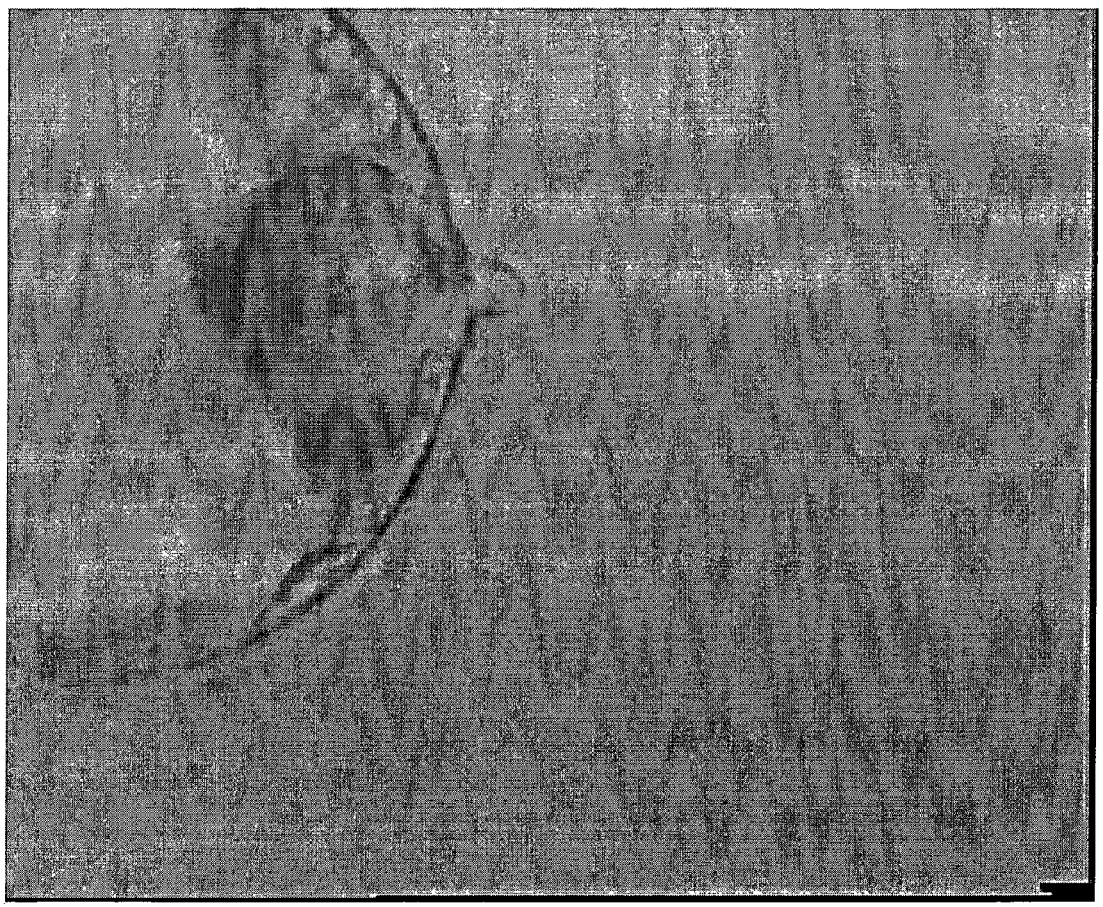
Figure 2C:
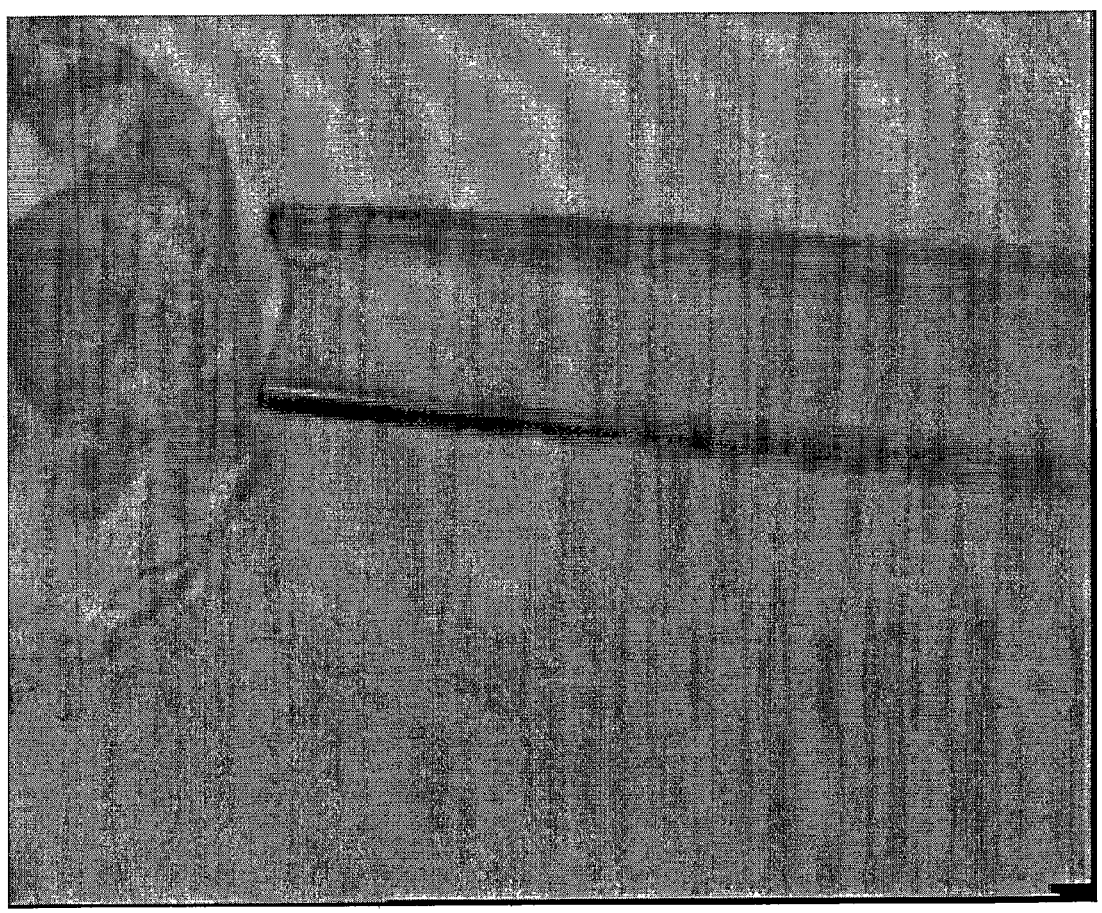
Figure 2D:
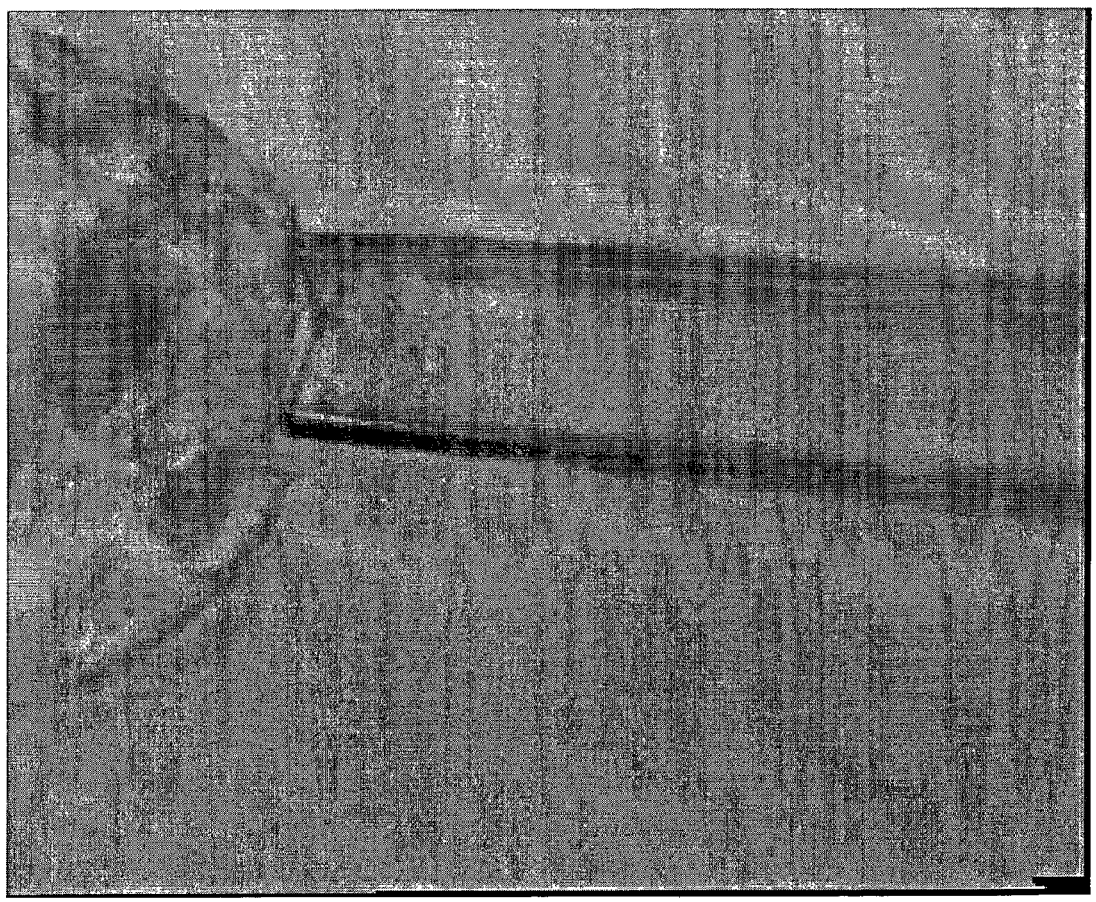
Figure 2E:
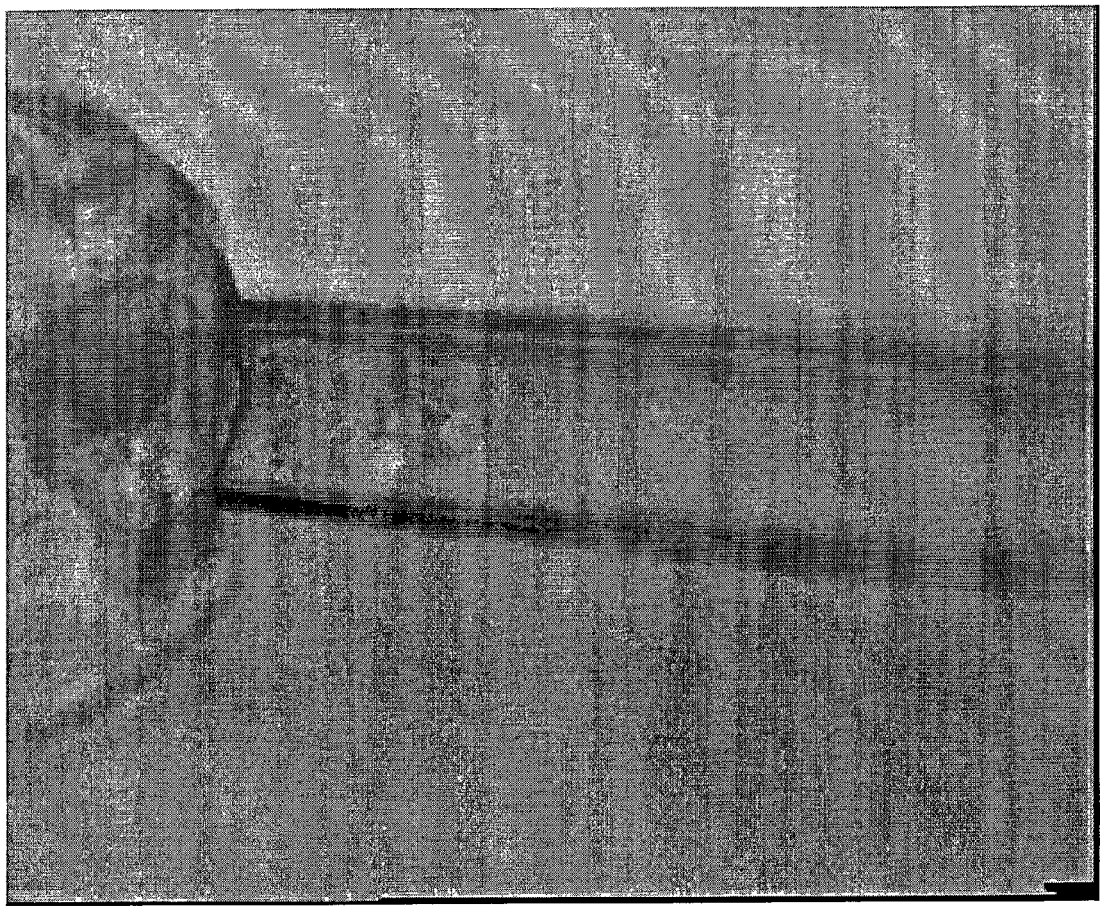
Figure 2F:
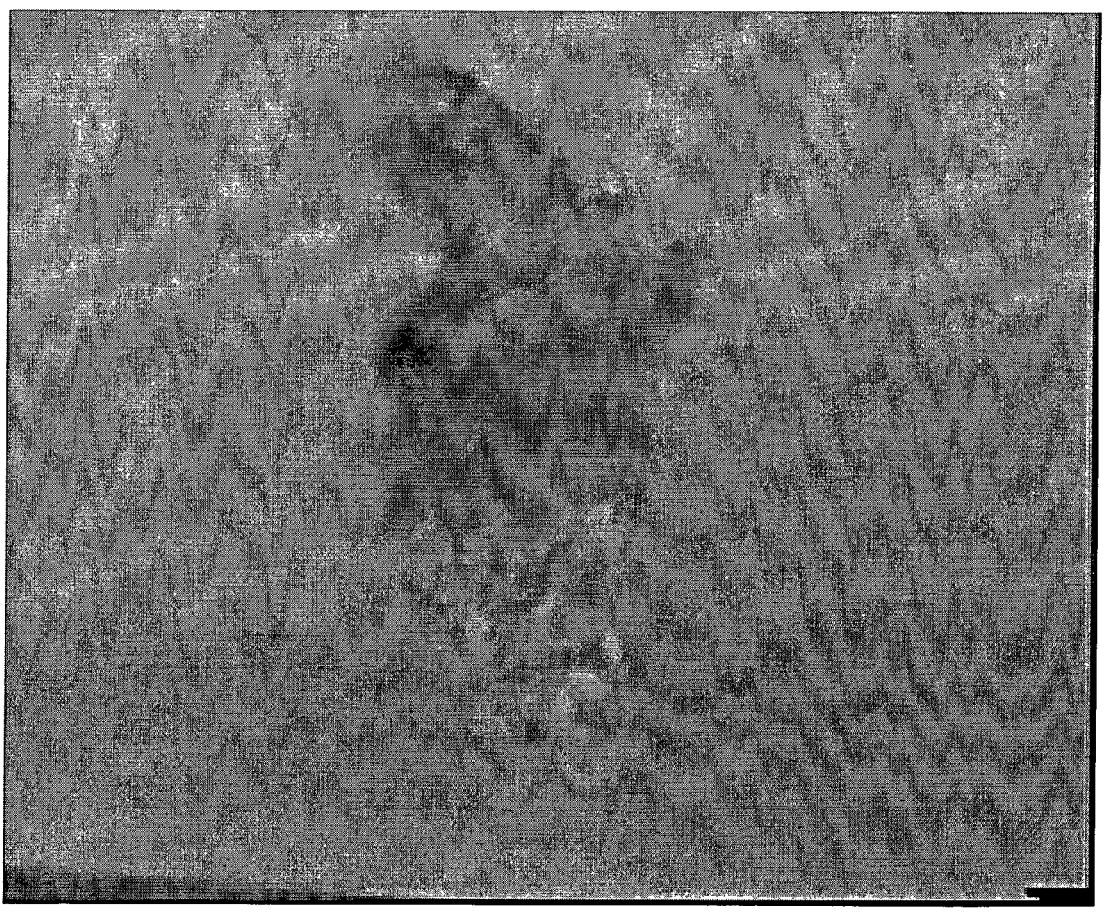
Figure 2G:
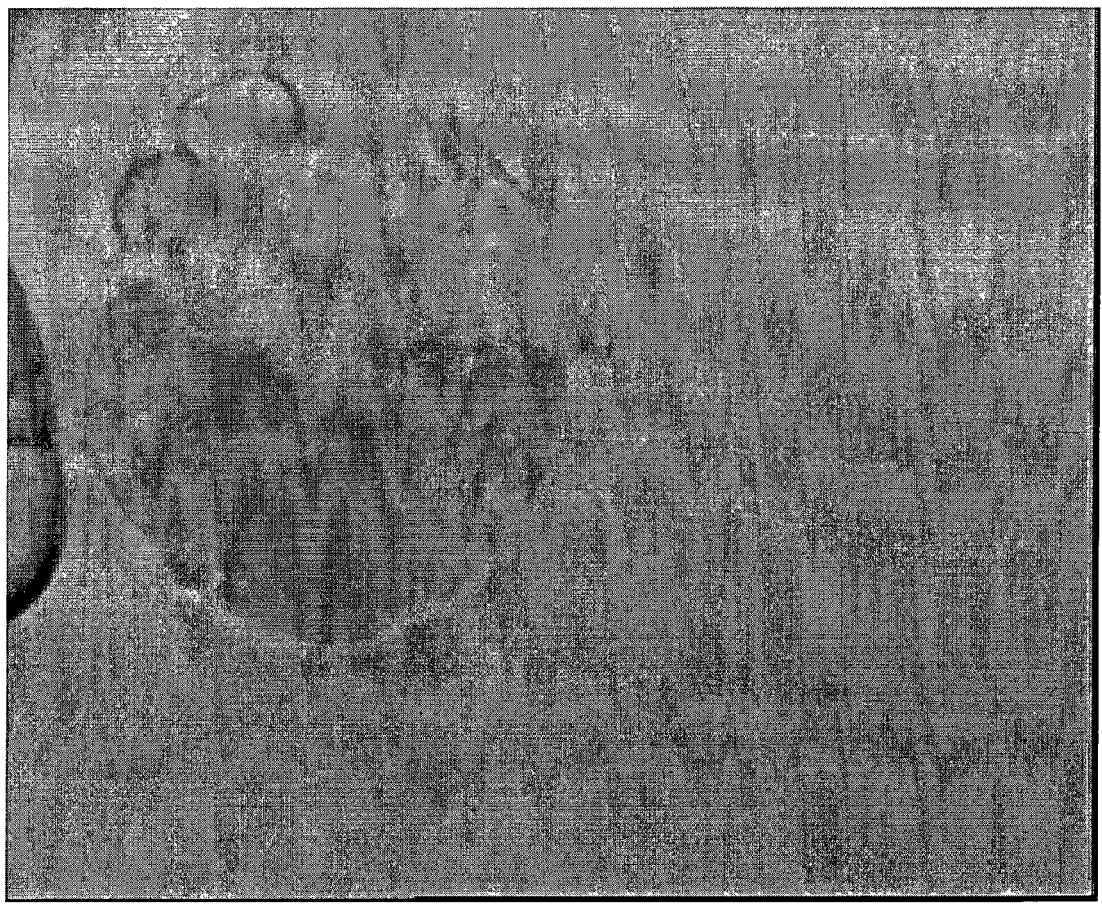
Figure 3A:
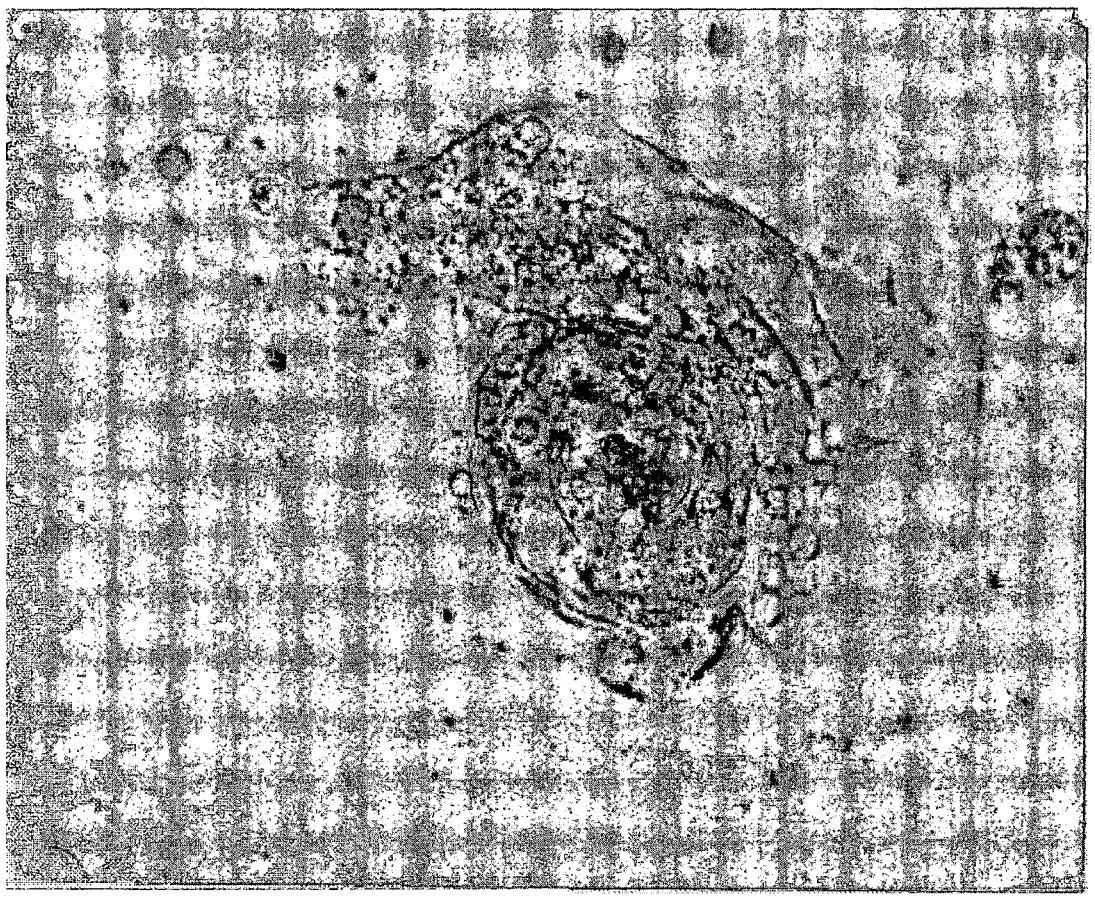
Figure 3B:
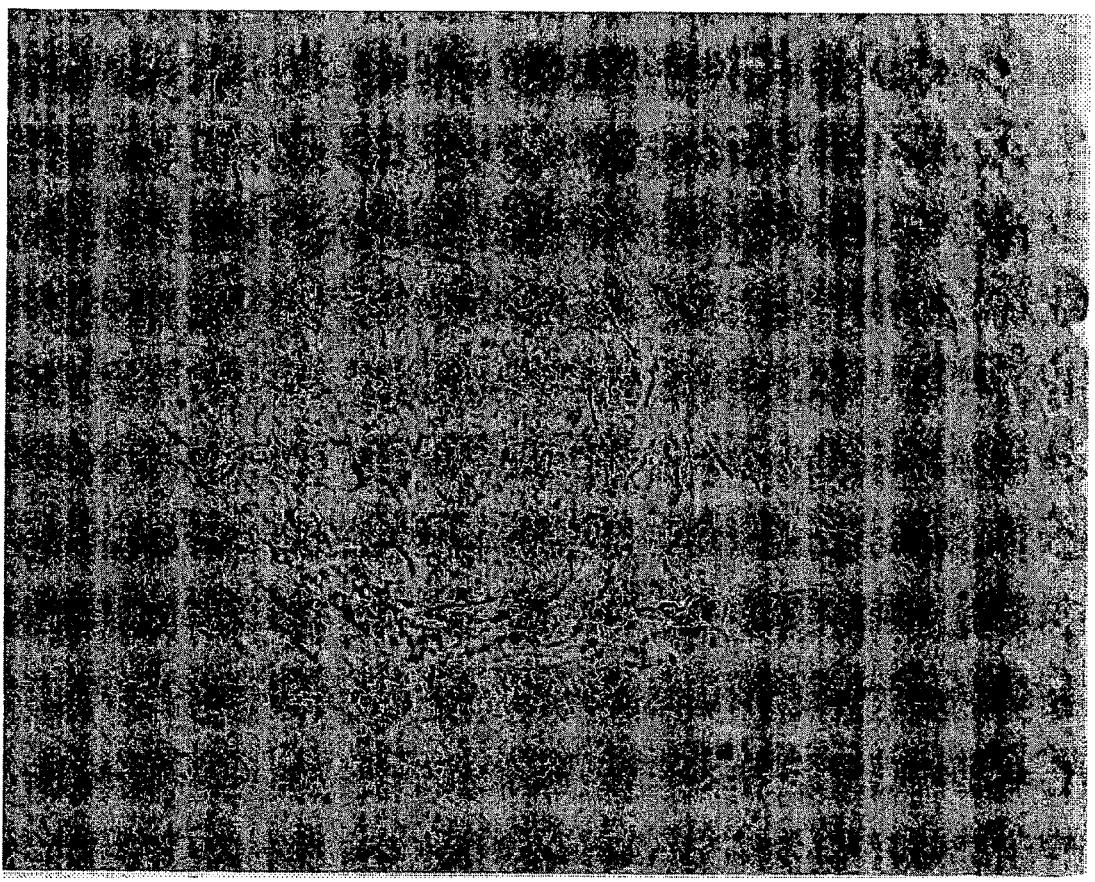

FIG. 3. (a) is a scanned image of isolated inner cell mass in culture seeded on primary mouse embryonic fibroblast feeder cells (day 3).

FIG. 3 (b) is a scanned image of isolated inner cell mass in culture on primary mouse embryonic fibroblast feeder cells (day 7)

Figure 4:
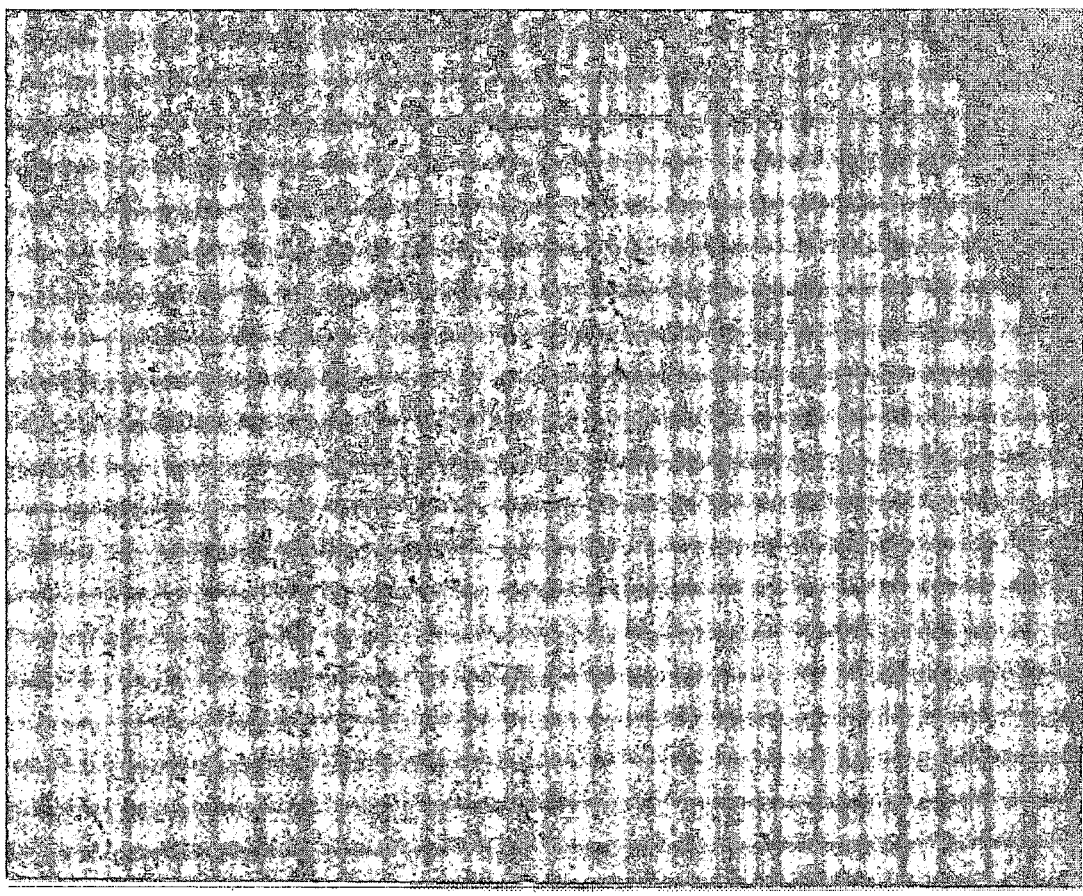

FIG. 4 is a scanned image of isolated ICM in culture on the primary mouse embryonic fibroblast feeder cells (day 5) another embryo.

Figure 5:
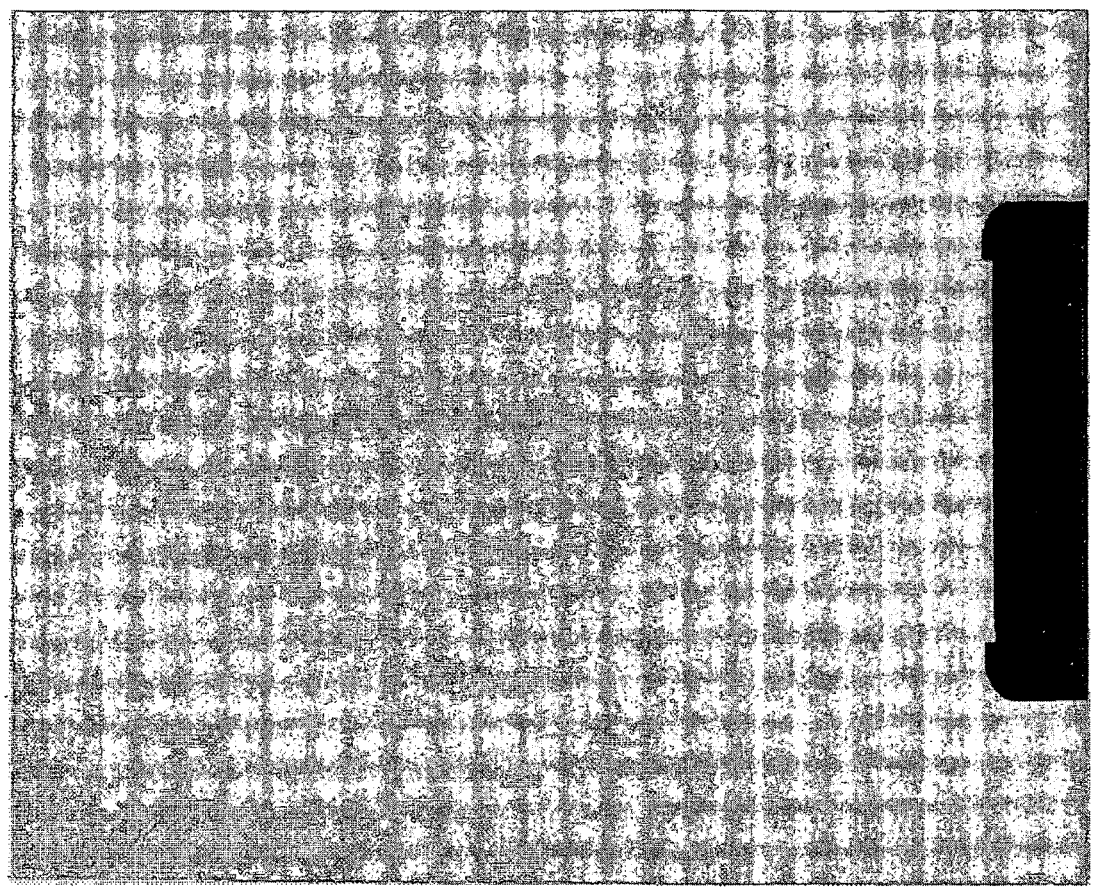

FIG. 5 is a scanned image of embryonic stem cell line derived from inner cell mass isolated by laser ablation method.

One skilled in the art will appreciate that the present invention is well adapted to carry out the objects and obtain the ends and advantages mentioned therein above. The instant invention has been shown and described herein in what is considered to be the most practical and preferred embodiment. It is recognized, that, departures may be made therefrom within the scope of the invention. It is to understood that the invention is not limited to the particulars disclosed and extends to all equivalents within the scope of the scope of the claims.

We claim:

1. A method for establishing a cell line from the inner cell mass of a human blastocyst, comprising the steps of:
   (a) isolating a blastocyst having a zona pellucida, a trophectoderm, and an inner cell mass;
   (b) creating an aperture in the blastocyst by laser ablation;
   (c) isolating cells from the inner cell mass from the blastocyst through the aperture; and
   (d) culturing the cells to establish a cell line.

2. The method of claim 1, wherein the aperture is through the zona pellucida.

3. The method of claim 1, wherein the aperture is through the zona pellucida and the trophectoderm.

4. The method of claim 1, wherein the laser ablation is achieved using a non-contact diode laser.

5. The method of claim 4, wherein the non-contact diode laser is a continuous 1.48 μm diode laser.

6. The method of claim 1, wherein cells from the inner cell mass are isolated by aspiration using an aspiration pipette introduced through the aperture.

7. The method of claim 1, wherein isolating cells from the inner cell mass is carried out in the absence of animal generated antibodies and sera.

8. A method for establishing a human embryonic stem cell line comprising the steps of:
   (a) isolating cells of an inner cell mass from an isolated blastocyst stage embryo by creating an aperture in the blastocyst stage embryo by laser ablation, and removing cells of the inner cell mass from the blastocyst stage embryo through the aperture;
   (b) culturing the cells of the inner cell mass in the presence of an embryonic stem cell medium and an inactivated feeder layer to produce inner cell mass derived masses; and
   (c) culturing the inner cell mass derived masses to produce an isolated human embryonic stem cell line.

9. The method of claim 8, wherein the embryonic stem cell medium comprises:
   (a) Dulbecco's modified Eagle's medium without sodium pyruvate;
   (b) fetal bovine serum in an amount from 10% to 30% of the volume of the embryonic stem cell medium;
   (c) beta-mercaptoethanol;
   (d) non-essential amino acids;
   (e) L-glutamine; and
   (f) basic fibroblast growth factor.

10. The method of claim 8, further comprising mechanically dissociating the inner cell mass derived masses of step (b) and re-plating the mechanically dissociated cells of the inner cell mass derived masses on a feeder layer.

11. The method of claim 1, wherein the isolated blastocyst of step (a) is placed in conventional Embryo biopsy medium.

12. The method of claim 11, wherein the Embryo biopsy medium is Ca++/Mg++ free.

13. The method of claim 1, further comprising a micromanipulator system comprising a microscope with a heating stage, a holding pipette, an aspiration pipette, and an air syringe, wherein the isolated blastocyst of step (a) is placed on the heating stage, the micromanipulator system is adjusted so that the blastocyst is at the center of the microscope field, and the blastocyst is secured with the holding pipette by suction through the air syringe, so that the inner cell mass is opposite the holding pipette.

14. The method of claim 2, wherein the aperture is generated by laser ablation using a 1.48 μm diode laser.

15. The method of claim 3, wherein the aperture is generated by laser ablation using a 1.48 μm diode laser, and is adjacent to the inner cell mass.

16. The method of claim 6, wherein the cells of the inner cell mass are washed one or more times in embryonic stem cell media, and placed on a feeder layer in the presence of embryonic stem cell media.

17. The method of claim 16, where in the feeder layer is of murine or human origin.

18. The method of claim 16, where in the feeder layer is an embryonic fibroblast feeder layer.

19. The method of claim 1, wherein the isolated blastocyst is the product of in vitro fertilization.

20. The method of claim 1, wherein the isolated blastocyst is the product of intracytoplasmic sperm injection.

21. The method of claim 8, where in the feeder layer is of murine or human origin.

22. The method of claim 8, wherein the feeder layer is an embryonic fibroblast feeder layer.

23. The method of claim 10, where in the feeder layer is of murine or human origin.

24. The method of claim 10, wherein the feeder layer is an embryonic fibroblast feeder layer.

25. A method of establishing a human embryonic stem cell line, comprising the steps of:
   (a) isolating a human blastocyst comprising an inner cell mass;
   (b) creating an aperture in the blastocyst by laser ablation;
   (c) isolating cells from the inner cell mass of the blastocyst through the aperture;
   (d) culturing the cells to obtain an isolated human embryonic stem cell line.

26. The method of claim 25, wherein the aperture is through the zona pellucida and the trophectoderm.

27. The method of claim 25, wherein the laser ablation is achieved using a non-contact diode laser.

28. The method of claim 25, wherein cells of the inner cell mass are isolated by aspiration through the aperture.

29. The method of claim 25, wherein the human embryonic stem cell line is established in the absence of animal generated antibodies and sera.

30. The method of claim 25, wherein step (c) further comprises plating the cells of the inner cell mass on a feeder layer, wherein inner cell mass-derived cell masses are formed.

31. The method of claim 30, wherein the feeder layer is an embryonic fibroblast feeder layer.

32. The method of claim 30, where in the feeder layer is of murine or human origin.

33. The method of claim 30, wherein the inner cell mass-derived cell masses are dissociated and replated on a feeder layer.

* * * * *